(12) United States Patent
Okada

(10) Patent No.: US 10,561,430 B2
(45) Date of Patent: Feb. 18, 2020

(54) BASKET TYPE GRASPING FORCEPS

(71) Applicant: OLYMPUS CORPORATION, Hachioji-shi, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 282 days.

(21) Appl. No.: 15/139,992

(22) Filed: Apr. 27, 2016

(65) Prior Publication Data

US 2016/0235423 A1 Aug. 18, 2016

Related U.S. Application Data

(63) Continuation of application No. PCT/JP2014/079189, filed on Nov. 4, 2014.

(30) Foreign Application Priority Data

Nov. 12, 2013 (JP) .................................. 2013-233974

(51) Int. Cl.
*A61B 17/221* (2006.01)
*A61B 90/00* (2016.01)

(52) U.S. Cl.
CPC ............ *A61B 17/221* (2013.01); *A61B 90/03* (2016.02); *A61B 2017/2212* (2013.01); *A61B 2017/2215* (2013.01); *A61B 2090/037* (2016.02)

(58) Field of Classification Search
CPC . A61B 17/221; A61B 90/03; A61B 2090/037; A61B 2017/2212; A61B 2017/2215
See application file for complete search history.

(56) References Cited

U.S. PATENT DOCUMENTS

| 6,152,932 A | * | 11/2000 | Ternstrom | ............ | A61B 17/221 606/113 |
| 2004/0138677 A1 | * | 7/2004 | Little | ................... | A61B 17/221 606/127 |
| 2004/0236351 A1 | * | 11/2004 | Yanuma | ............... | A61B 17/221 606/127 |

FOREIGN PATENT DOCUMENTS

| DE | 10 2005 030 010 A1 | 12/2006 |
| EP | 2 638 870 A1 | 9/2013 |
| JP | H02-116411 U | 9/1990 |
| JP | H03-70111 U | 7/1991 |
| JP | H11-114070 A | 4/1999 |
| JP | 2004-516880 A | 6/2004 |

(Continued)

OTHER PUBLICATIONS

Feb. 10, 2015 Search Report issued in International Patent Application No. PCT/JP2014/079189.

*Primary Examiner* — Tan-Uyen T Ho
*Assistant Examiner* — Rachel S Highland
(74) *Attorney, Agent, or Firm* — Oliff PLC

(57) ABSTRACT

Basket type grasping forceps include a sheath, a main body section, and a manipulation section, the main body section includes a basket section and a manipulation wire, the basket section includes a plurality of basket wires and a distal fixing member fixed to the plurality of basket wires, and the distal fixing member has a wire-fixing section to which a first wire serving which is at least one of the plurality of basket wires is fixed, and a high-strength fixing section to which a second wire which is at least another one of the plurality of basket wires is fixed more strongly than a fixing strength of the first wire in the wire-fixing section.

7 Claims, 11 Drawing Sheets

(56) References Cited

FOREIGN PATENT DOCUMENTS

| | | |
|---|---|---|
| JP | 2006-094876 A | 4/2006 |
| JP | 2013-000219 A | 1/2013 |
| WO | 2004/064597 A2 | 8/2004 |
| WO | 2012/141213 A1 | 10/2012 |

* cited by examiner

BASKET TYPE GRASPING FORCEPS

This application is a continuation application based on PCT Patent Application No. PCT/JP2014/079189, filed Nov. 4, 2014, claiming priority based on Japanese Patent Application No. 2013-233974, filed Nov. 12, 2013, the content of which is incorporated herein by reference.

BACKGROUND OF THE INVENTION

Field of the Invention

The present invention relates to basket type grasping forceps.

Description of the Related Art

In the related art, basket type grasping forceps inserted into a duct line in a body such as a bile duct or the like and configured to collect foreign substances such as calculi or the like are known (for example, see Japanese Unexamined Patent Application, First Publication No. H11-114070, Japanese Unexamined Patent Application, First Publication No. 2006-94876, and PCT International Publication No. 2012/141213).

Since the basket type grasping forceps have a structure configured to hold foreign substances by a plurality of wires, when large foreign substances are to be collected, a basket may not be removed from the duct line while holding the foreign substances. In this case, the temporarily held foreign substances should be discharged from the basket in the duct line even to only remove the basket type grasping forceps. However, in such a case, since the foreign substances are large, once the foreign substances are held, the foreign substances may not be discharged to the outside of the basket in the duct line as an operator intends. For example, when the foreign substances are not removed from between the plurality of wires disclosed in Japanese Unexamined Patent Application, First Publication No. H11-114070, Japanese Unexamined Patent Application, First Publication No. 2006-94876, and PCT International Publication No. 2012/141213, the basket cannot be removed from the duct line.

Furthermore, when an excessive load is applied to the plurality of wires that constitute the basket, a portion at which the plurality of wires are bundled may be damaged and break the basket. Japanese Unexamined Utility Model Application, First Publication No. H02-116411 discloses a structure in which, as one of the plurality of wires is formed in a hook shape and is hooked to a manipulation wire for advancing and retracting the basket, the basket can be prevented from being completely removed and falling off from the manipulation wire when a proximal end of the basket is broken.

SUMMARY OF THE INVENTION

According to a first aspect of the present invention, Basket type grasping forceps according include a sheath; a main body section having a distal end and a proximal end and being inserted through the sheath; and a manipulation section fixed to the sheath and at which the proximal end of the main body section is disposed, wherein the main body section comprises: a basket section disposed at the distal end side of the main body section and configured to hold foreign substances; and a manipulation wire disposed at a proximal end side of the basket section and fixed to the basket section, wherein the basket section comprises: a plurality of basket wires disposed to form a basket shape to hold the foreign substances therein; and a distal fixing member fixed to the plurality of basket wires at a distal end portion of the basket section, and the distal fixing member has a wire-fixing section to which a first wire which is at least one of the plurality of basket wires is fixed, and a high-strength fixing section to which a second wire which is at least another one of the plurality of basket wires is fixed more strongly than a fixing strength of the first wire in the wire-fixing section, the basket section further includes a center wire extending from a distal end of the basket section toward a proximal side of the basket section; and the distal fixing member further includes: a first distal fixing member fixed to the basket wire and disposed at a distal side of the basket section; and a second distal fixing member having the high-strength fixing section and disposed at a distal side of the first distal fixing member, at least one of the plurality of basket wires are fixed to the high-strength fixing section, the second distal fixing member being fixed to a distal end of the center wire.

According to a second aspect of the present invention, in the basket type grasping forceps according to the first aspect, the first distal fixing member may have a first hole into which the first wire is inserted; and a second hole spaced from the first hole via a partition section and into which the second wire is inserted.

According to a third aspect of the present invention, in the basket type grasping forceps according to the first aspect, the wire-fixing section may have a first fixing agent that connects the first wire and the distal fixing member, and the high-strength fixing section may have a second fixing agent that connects the second wire and the distal fixing member and is different from the first fixing agent.

According to a fourth aspect of the present invention, in the basket type grasping forceps according to the third aspect, the first fixing agent may be an adhesive agent and the second fixing agent may be a brazing material or solder.

According to a fifth aspect of the present invention, in the basket type grasping forceps according to the third aspect, the first fixing agent may be solder and the second fixing agent may be a brazing material or an adhesive agent.

According to a sixth aspect of the present invention, in the basket type grasping forceps according to the second aspect, the high-strength fixing section may further have a locking portion to which the second wire is locked.

DETAILED DESCRIPTION OF THE PREFERRED EMBODIMENTS

First Embodiment

Figure 1:
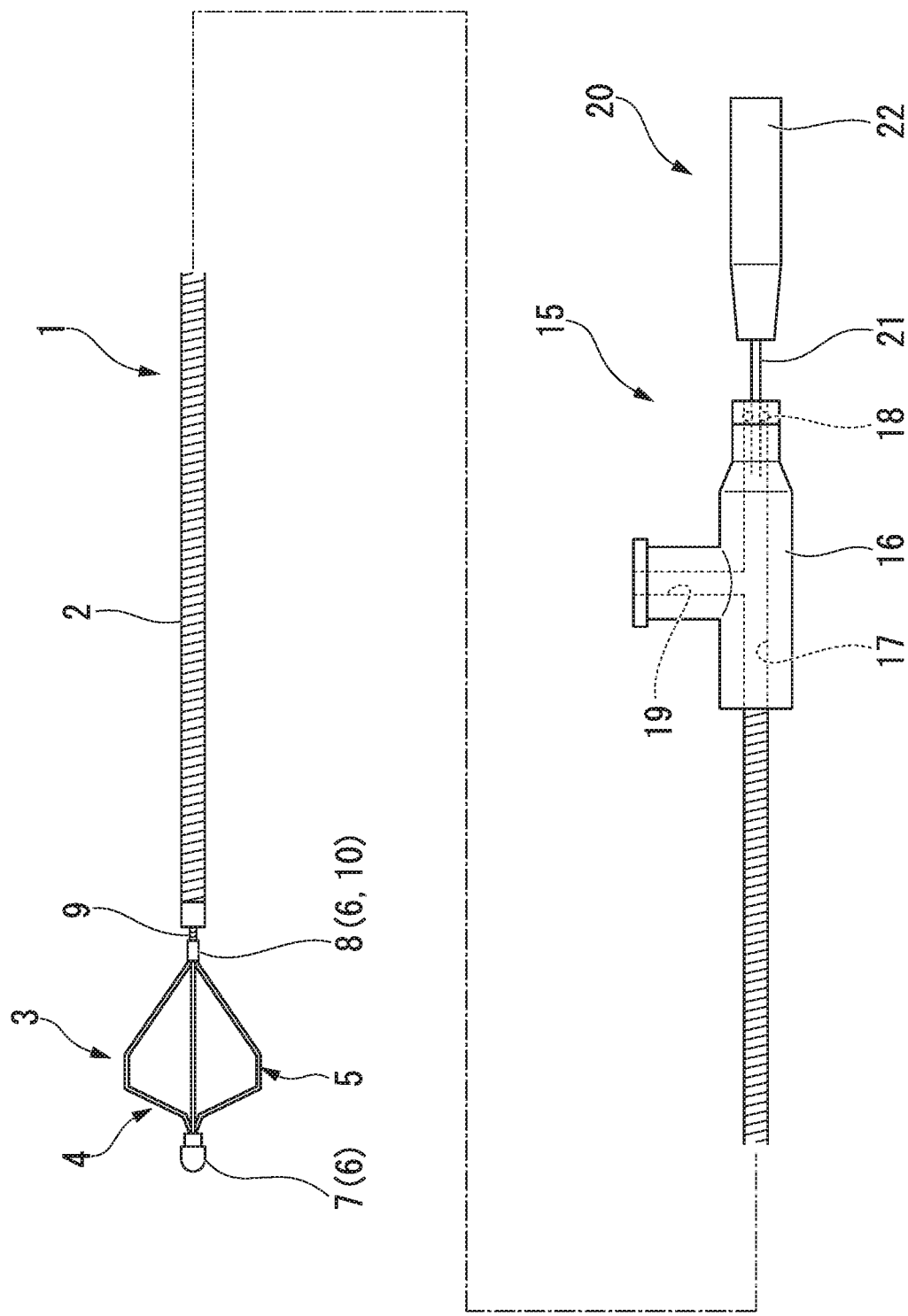
FIG. 1 is a side view showing basket type grasping forceps according to a first embodiment of the present invention.
Figure 2:
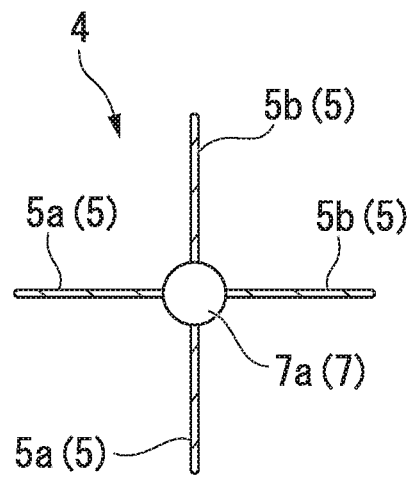
FIG. 2 is a front view of a distal portion of a main body section of the basket type grasping forceps according to the first embodiment of the present invention.
Figure 3:
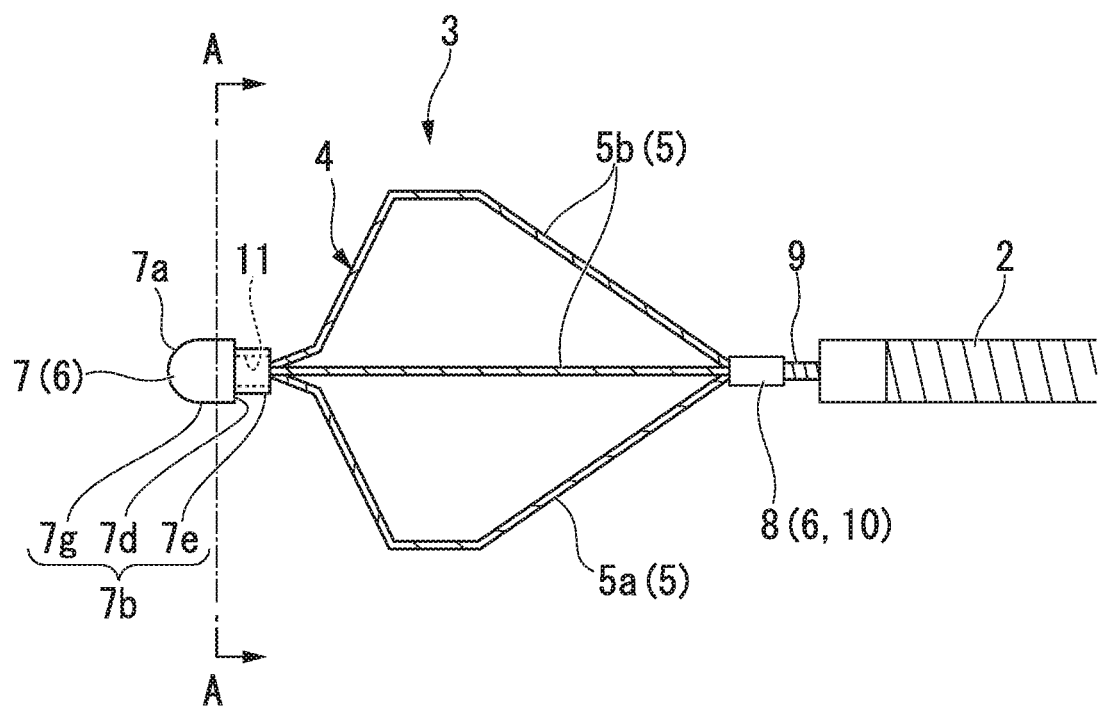
FIG. 3 is an enlarged view showing the distal portion of the basket type grasping forceps according to the first embodiment of the present invention.
Figure 4:
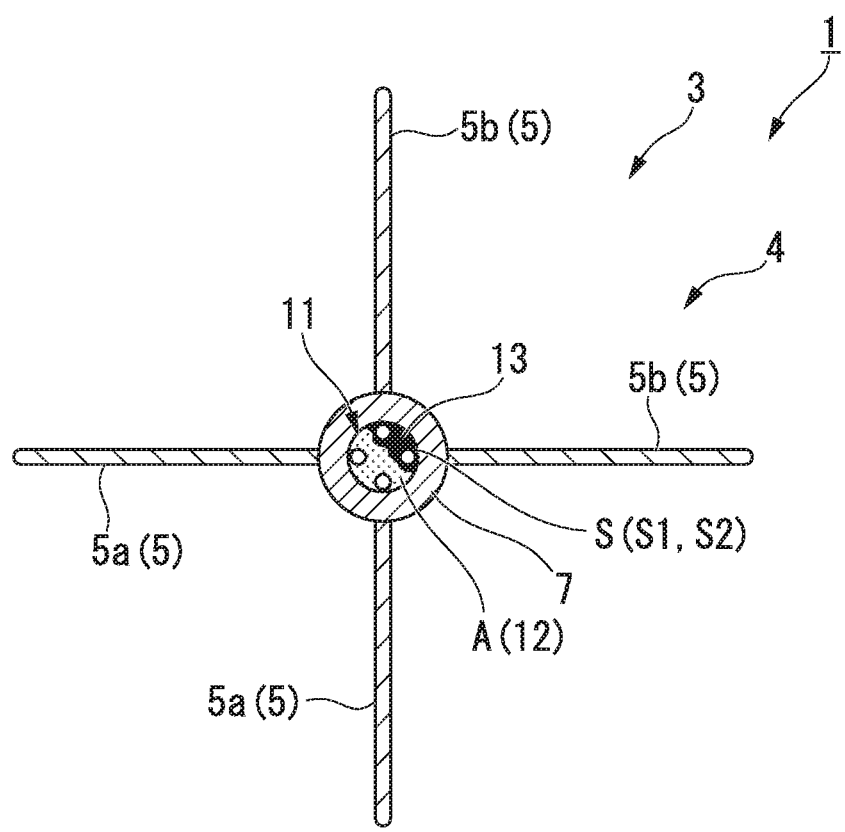
FIG. 4 is a cross-sectional view taken along line A-A of FIG. 3.

Basket type grasping forceps according to a first embodiment of the present invention will be described. FIG. 1 is a side view showing basket type grasping forceps 1 according to the embodiment. FIG. 2 is a front view of the basket type grasping forceps 1 according to the embodiment. FIG. 3 is an enlarged view showing a distal portion of the basket type grasping forceps 1 according to the embodiment. FIG. 4 is a cross-sectional view taken along line A-A of FIG. 3.

As shown in FIG. 1, the basket type grasping forceps 1 includes a sheath 2, a main body section 3 and a manipulation section 15.

The sheath 2 is a tubular member having flexibility. An external dimension of the sheath 2 is set such that the sheath 2 can be inserted through a treatment tool channel of an endoscope to freely advance and retract. A distal end part of the sheath 2 has hardness such that the sheath 2 can fold a basket section 4 (to be described below) when using the basket type grasping forceps 1. In addition, the sheath 2 may be constituted by a coil or the like in which a metal wire is wound in a helical shape that provides both strength to endure a compressive force received from the basket section 4 when the basket section 4 is folded and flexibility to curve to follow the treatment tool channel.

The main body section 3 is an elongated member having a distal end and a proximal end and inserted through the sheath 2.

As shown in FIGS. 1 and 3, the main body section 3 includes the basket section 4, a manipulation wire 9 and a connecting member 10.

As shown in FIGS. 1 and 2, the basket section 4 is disposed at a distal side of the main body section 3. The basket section 4 is capable of spreading in a basket shape to hold foreign substances and is expandable. The basket section 4 is a substantially linear shape that can be accommodated in the sheath 2 in a contracted state.

The basket section 4 includes a plurality of basket wires 5, and a fixing member 6 configured to fix the plurality of basket wires 5 in a basket shape.

The basket wires 5 include a plurality of wires (a first wire 5a and a second wire 5b) disposed to form a basket shape such that foreign substances are held therein.

Both of the first wire 5a and the second wire 5b are wires having elasticity, and an initial state thereof is set to spread in the basket shape in a state in which an external force is not applied. While details will be described below, in the embodiment, the first wire 5a and the second wire 5b are different from each other in that the first wire 5a is fixed to a wire-fixing section 12 of a distal fixing member 7 and the second wire 5b is fixed to a high-strength fixing section 13 of the distal fixing member 7. Materials and shapes of the first wire 5a and the second wire 5b may be equal to each other.

In the embodiment, the basket wires 5 are constituted by two neighboring first wires 5a and two neighboring second wires 5b.

The fixing member 6 shown in FIG. 3 has the distal fixing member 7 and a proximal fixing member 8. The basket wires 5 are bundled and fixed to the distal fixing member 7 at a distal side of the basket section 4. The basket wires 5 are bundled and fixed to the proximal fixing member 8 at a proximal side of the basket section 4. In the embodiment, the proximal fixing member 8 also functions as the connecting member 10 configured to connect the basket section 4 and the manipulation wire 9.

As shown in FIGS. 3 and 4, the distal fixing member 7 is fixed to the plurality of basket wires 5 at an end portion of the distal end side of the basket section 4. The distal fixing member 7 is a substantially cylindrical member and having a distal end portion 7a, an outer circumferential portion 7b and a hole section 11.

The distal end portion 7a is configured to have a curved surface in order to avoid damaging the biological tissue when the distal end portion 7a comes in contact with the biological tissue.

The outer circumferential portion 7b has a large diameter section 7g, a step difference 7d and a small diameter section 7e formed in sequence from the distal side.

An outer diameter of the large diameter section 7g is larger than an inner surface of the sheath 2 and substantially equal to an outer diameter of the sheath 2, and is set a size of which an outer surface of the large diameter section 7g is substantially flush with an outer surface of the sheath 2 in a state in which the distal fixing member 7 is engaged with the distal end of the sheath 2. The stepped difference 7d has a surface that abuts a distal end surface of the sheath 2. The small diameter section 7e has a diameter substantially equal to that of the inner surface of the sheath 2 or smaller than that of the inner surface of the sheath 2.

The hole section 11 has the wire-fixing section 12 to which the first wire 5a is fixed and the high-strength fixing section 13 to which the second wire 5b is fixed. In the embodiment, the wire-fixing section 12 is a region to which the first wire 5a is fixed in an inner space of the distal fixing member 7. The high-strength fixing section 13 is a region to which the second wire 5b is fixed in the inner space of the distal fixing member 7.

The wire-fixing section 12 fixes the first wire 5a to the hole section 11 with an adhesive agent A serving as a first fixing agent. The adhesive agent A is, for example, an epoxy-based adhesive agent A.

The high-strength fixing section 13 is a portion configured to fix the second wire 5*b* to the hole section 11 with a fixing strength strongly than a fixing strength of the first wire 5*a* with respect to the wire-fixing section 12. The high-strength fixing section 13 fixes the second wire 5*b* to the hole section 11 using a solder adhesive S as a second fixing agent. The solder adhesive S is, for example, a brazing material S1, solder S2, or the like.

In the embodiment, the second wire 5*b* is inserted into the hole section 11 and the second wire 5*b* is fixed to a portion of an inner surface of the hole section 11 using the solder S, and then, the first wire 5*a* is inserted into the hole section 11 and the adhesive agent A is filled into the hole section 11, thereby, the wire-fixing section 12 and the high-strength fixing section 13 can be installed in the single hole section 11.

Since the proximal fixing member 8 shown in FIG. 3 is formed in a cylindrical shape. The basket wires 5 are inserted into the proximal fixing member 8 from the distal side, thereby the basket wires 5 are bounded. A fixing method of the basket wires 5 to the proximal fixing member 8 may be appropriately selected from known methods based on fixing methods of the distal fixing member 7 and the basket wires 5 such as welding, caulking, brazing, soldering, adhesion, and so on. That is, in the embodiment, a fixing strength between the proximal fixing member 8 and the basket wires 5 is larger than a fixing strength between the wire-fixing section 12 and the basket wires 5 in the distal fixing member 7.

The manipulation wire 9 is a wire disposed at the proximal side of the basket section 4 and fixed to the proximal fixing member 8 of the basket section 4.

The connecting member 10 is a cylindrical member configured to fix the basket section 4 and the manipulation wire 9. The fixing strength between the basket section 4 and the connecting member 10 is larger than the fixing strength between the basket wires 5 and the wire-fixing section 12. The fixing strength between the manipulation wire 9 and the connecting member 10 is larger than the fixing strength between the basket wires 5 and the wire-fixing section 12. In the embodiment, the connecting member 10 and the proximal fixing member 8 are formed integrally.

As shown in FIG. 1, the manipulation section 15 is fixed to a proximal end of the sheath 2 and a proximal end of the main body section 3 is disposed thereat.

The manipulation section 15 includes a manipulation main body 16 and a slider 20.

The manipulation main body 16 includes a first port 17 in which the slider 20 is disposed, and a second port 19 in communication with the inner space of the sheath 2.

The first port 17 has a straight hole having a center line on an extension line of a center line of the sheath 2. A branch in communication with the second port 19 is formed in an intermediate portion of the first port 17. The first port 17 has an O-ring 18 which is in watertight contact with a shaft 21 (to be described below).

The second port 19 is in communication with the intermediate portion of the first port 17, and is capable of communicating with the inner space of the sheath 2 via the first port 17. The second port 19 is installed at the manipulation main body 16 to perform a procedure of ejecting a liquid such as a contrast medium or the like from the distal end of the sheath 2.

The slider 20 includes the shaft 21 and a grip 22. The shaft 21 is fixed to a proximal end of the manipulation wire 9. The grip 22 is fixed to a proximal end of the shaft 21. In the embodiment, the basket section 4 can be inserted into and removed from the opening of the distal end of the sheath 2 by gripping the grip 22 to advance and retract the shaft 21 with respect to the first port 17 by an operator.

Figure 5:
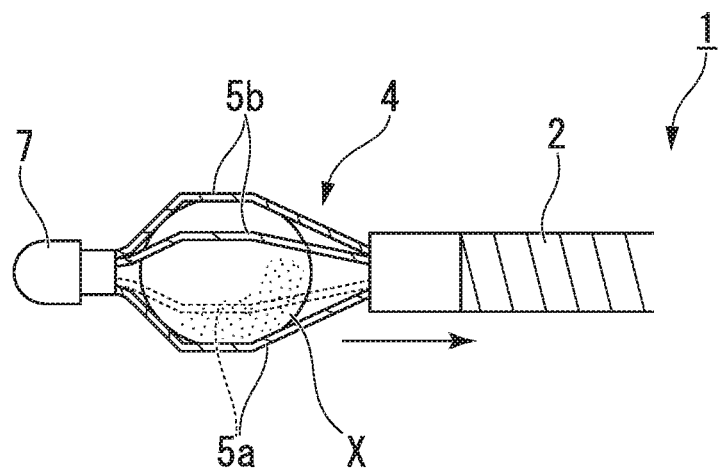
FIG. 5 is a view describing an action of the basket type grasping forceps according to the first embodiment of the present invention.
Figure 6:
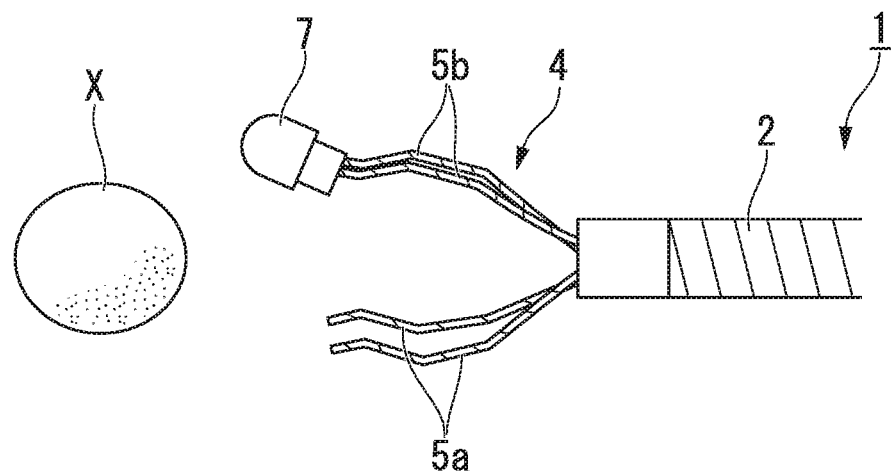
FIG. 6 is a view describing the action of the basket type grasping forceps according to the first embodiment of the present invention.

Next, an action of the basket type grasping forceps 1 according to the embodiment will be described. FIGS. 5 and 6 are views describing the action of the basket type grasping forceps 1 according to the embodiment.

As shown in FIG. 5, like a conventional basket type medical treatment tool, the basket type grasping forceps 1 are inserted into a lumen such as a bile duct or the like in a patient's body through an endoscope channel in a state in which the basket section 4 is accommodated in the sheath 2. When the basket section 4 protrudes from the sheath 2 in the duct line by an advance operation of the slider 20, the basket section 4 is widely opened by an elastic force of the basket wires 5. After foreign substances X such as calculi or the like are introduced into the widely opened basket section 4, as the operator pulls the slider 20, the base end side of the basket section 4 may be pulled into the sheath 2 to reduce a diameter of the basket section 4. As a result, the foreign substances X may be tightly held in the basket. After that, the basket type grasping forceps 1 is removed from the patient's body together with the endoscope to collect the foreign substances X.

When the basket type grasping forceps 1 cannot be removed from the lumen in a state in which the foreign substances X are held in the basket section 4, when the basket section 4 is completely exposed from the opening of the distal end of the sheath 2 and the basket wires 5 is widen maximally, the foreign substances X can be discharged from the gaps of the basket wires 5 to the outside of the basket. However, when the foreign substances X cannot be discharged even in a state in which the basket wires 5 are maximally widened, the basket section 4 may be intentionally broken by the following manipulation.

In the embodiment, in order to break the basket section 4, first, as the operator of the basket type grasping forceps 1 moves the grip 22 of the slider 20 shown in FIG. 1 to the proximal side (a hand side), the basket section 4 is gradually accommodated in the sheath 2 from the proximal end of the basket section 4 (see FIG. 5). Accordingly, the basket wires 5 that constitute the basket section 4 are contracted. When the basket wires 5 are contracted from the proximal side, the foreign substances X in the basket section 4 are pushed and moved from the proximal side to the distal side of the basket section 4, or the foreign substances X are meshed into the gaps of the basket wires 5 and fixed their movement in a gap of the basket wires 5.

The operator further pulls the grip 22 of the slider 20 shown in FIG. 1 toward the proximal side (the hand side). When the operator further pulls the grip 22 of the slider 20 toward the proximal side, each of the basket wires 5 is pulled toward the proximal side. Here, since the foreign substances X are present in the basket section 4, the basket section 4 cannot be accommodated in the sheath 2. That is, as the grip 22 of the slider 20 is further pulled toward the proximal side (the hand side), the distal end of the sheath 2 presses the foreign substances X toward the distal side and each of the basket wires 5 is pulled toward the proximal side by the manipulation wire 9 in the basket section 4. That is, a force further pulling the grip 22 of the slider 20 toward the proximal side (the hand side) becomes a force pulling out each of the basket wires 5 from the distal fixing member 7.

Among the basket wires 5, the first wire 5*a* fixed to the wire-fixing section 12 shown in FIG. 4 is removed from the distal fixing member 7 prior to the second wire 5b fixed to the high-strength fixing section 13. Accordingly, the basket section 4 is broken at the distal end thereof, and as shown in FIG. 6, the basket section 4 having the basket shape is released at a portion surrounded by the first wire 5a.

When the manipulation wire 9 is further pulled toward the proximal side in a state in which the first wire 5a is removed from the wire-fixing section 12, the second wire 5b maintained in a fixed state at the high-strength fixing section 13 moves by receiving a force from an open end portion of the distal end of the sheath 2 to move the foreign substances X toward the first wire 5a. Accordingly, the foreign substances X present in the basket section 4 are pushed out to the outside of the basket section 4 from a portion at which fixation between the first wire 5a and the distal fixing member 7 is removed.

Further, after the foreign substances X are pushed out to the outside of the basket section 4, the first wire 5a and the second wire 5b are pulled into the sheath 2. Then, the distal fixing member 7 fixed to the distal end of the second wire 5b is fitted into the opening of the distal end of the sheath 2 to become a lid with respect to the distal end of the sheath 2. In this state, since both of the first wire 5a and the second wire 5b are pulled into the sheath 2, the distal end of the first wire 5a does not come in contact with biological tissue.

The basket type grasping forceps 1 in which the basket section 4 is broken and from which the foreign substances X are discharged is pulled out of the body together with the endoscope and discharged.

In order to remove the foreign substances X from the basket in the basket type medical treatment tool of the related art inside the lumen, operations such as introducing a crushing apparatus or the like into the body and crushing the foreign substances X, are necessary.

However, introduction of the grasping forceps or the like into the body on purpose of discharging the foreign substances X held in the basket from the inside of the lumen is inefficient.

Further, in the basket type medical treatment tool of the related art, when the wire is removed from a member configured to fix the wire at the proximal side of the basket, the proximal end of the wire is directed toward the proximal side in the body. For this reason, in a process of pulling the basket back toward the proximal side to extract the basket to the outside of the body, the proximal end of the wire may hurt biological tissue, and thus, careful manipulation is needed to prevent the removed wire from coming in contact with the biological tissue or the like.

In the basket type grasping forceps 1 according to the embodiment, when the basket is intentionally broken, since the distal fixing member 7 configured to fix each of the basket wires 5 at the distal end of the basket section 4 is broken earlier than the proximal fixing member 8, an opening is generated in a portion of the basket at the distal side of the basket section 4.

The wire-fixing section 12 and the high-strength fixing section 13 having different fixing strengths with respect to the basket wires 5 are installed at the distal fixing member 7. For this reason, when the operator pulls the manipulation wire 9 such that the first wire 5a is removed from the wire-fixing section 12, a gap sufficient to push out the foreign substances X to the outside of the basket section 4 is formed, and the distal fixing member 7 is held at the second wire 5b. For this reason, even when the basket section 4 is intentionally broken, the distal fixing member 7 or the like is not dropped into the body.

In addition, in the basket type grasping forceps 1 according to the embodiment, the basket wires 5 removed by manipulation of intentionally breaking the basket section 4 is removed from the distal fixing member 7 in a state in which the distal end of the basket wires 5 are directed toward the distal side, and the proximal end is held while being fixed to the proximal fixing section. For this reason, when the basket section 4 is pulled out to the outside of the body, the distal ends of the basket wires 5 hardly piercing the biological tissue, and the basket wires 5 removed from the distal fixing member 7 can be easily accommodated in the sheath 2.

In the embodiment, instead of the above-mentioned configuration, the following configuration may be provided.

In the embodiment, while an example in which the adhesive agent A is used in the wire-fixing section 12 and the solder adhesive S is used in the high-strength fixing section 13 has been described, fixing means in the wire-fixing section 12 and the high-strength fixing section 13 are not limited thereto. For example, both a solder adhesive S applied to the wire-fixing section 12 and the solder adhesive S applied to the high-strength fixing section 13 may be selected such that a fixing strength in the high-strength fixing section 13 is larger than that in the wire-fixing section 12 according to the material of the basket wires 5.

Specifically, when the first wire 5a is formed of stainless steel, the solder S2 may be used as the solder adhesive S for fixing the first wire 5a and the wire-fixing section 12, and the brazing material S1 may be used as the solder adhesive S configured to fix the second wire 5b and the high-strength fixing section 13.

In addition, the first wire 5a and the second wire 5b may be formed of different materials. For example, the first wire 5a formed of an NT alloy is fixed with solder or an adhesive agent and the second wire 5b formed of stainless steel is fixed with brazing, thereby the fixing strength of the high-strength fixing section 13 may be larger than that of the wire-fixing section 12.

Second Embodiment

Figure 7:
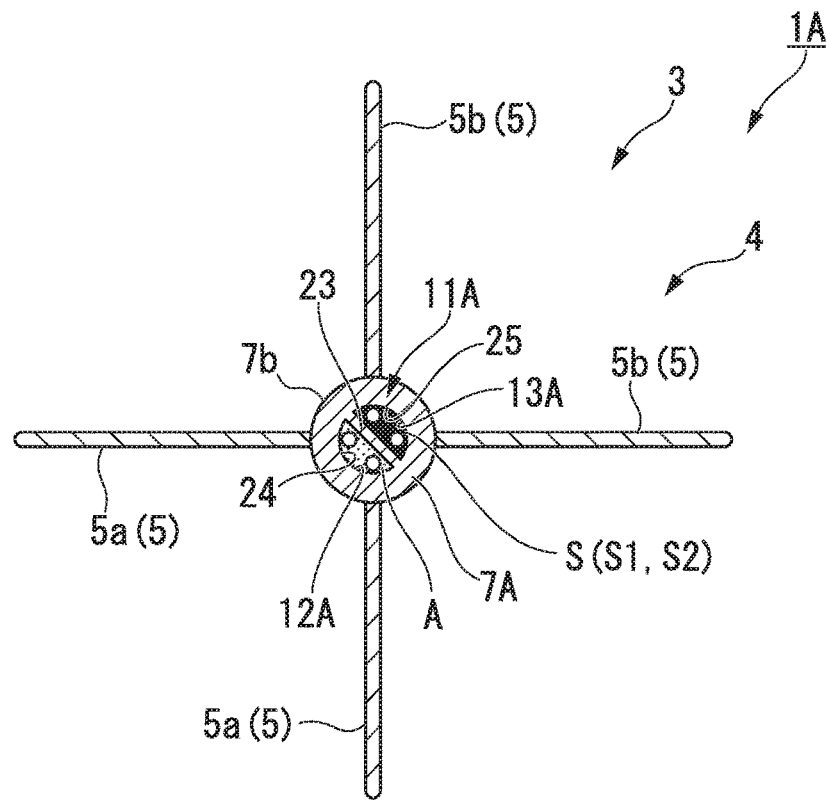
FIG. 7 is a cross-sectional view taken along the same line as the line A-A of FIG. 3, showing basket type grasping forceps according to a second embodiment of the present invention.

Next, a second embodiment of the present invention will be described. In the embodiment, the same reference numerals as the first embodiment designate components that are common in shapes or functions to the components described in the first embodiment, and overlapping description thereof will be omitted. FIG. 7 is a cross-sectional view taken along the same line A-A of FIG. 3, showing basket type grasping forceps 1A according to the embodiment.

As shown in FIG. 7, the basket type grasping forceps 1A according to the embodiment includes a distal fixing member 7A having a shape different from the distal fixing member 7 described in the first embodiment.

The distal fixing member 7A has the same outer circumferential portion 7b as the distal fixing member 7 described in the first embodiment. The distal fixing member 7A includes a hole section 11A having a shape different from the hole section 11 described in the first embodiment.

The hole section 11A includes a wire-fixing section 12A, a high-strength fixing section 13A and a partition section 23. That is, the hole section 11A has a first hole 24 and a second hole 25. The first hole 24 is the wire-fixing section 12A into which the first wire 5a is inserted. The second hole 25 is the high-strength fixing section 13A spaced from the first hole 24 via the partition section 23 and into which the second wire 5b is inserted.

The first hole 24 is a hole into which the first wire 5a that is a portion of the plurality of wires constituting the basket wires 5 is inserted. The first hole 24 of the embodiment is a through-hole passing through the distal fixing member 7A. The adhesive agent A configured to fix the first wire 5a and the distal fixing member 7A is filled in the first hole 24. The adhesive agent A filled in the first hole 24 is, for example, an epoxy-based adhesive agent A.

The second hole 25 is a hole into which a wire except for the first wire 5a among the plurality of wires constituting the basket wires 5 is inserted. The second hole 25 of the embodiment is a through-hole passing through the distal fixing member 7A. The solder adhesive S configured to fix the second wire 5b and the distal fixing member 7A is filled in the second hole 25. The solder adhesive S filled in the second hole 25 is, for example, the brazing material S1 or the solder S2.

That is, in the embodiment, the fixing strength between the second wire 5b and the distal fixing member 7A in the second hole 25 is larger than the fixing strength between the first wire 5a and the distal fixing member 7A in the first hole 24.

The partition section 23 separates the first hole 24 and the second hole 25. Since the holes are independently formed by providing the partition section 23 at the distal fixing member 7A, for example, the solder adhesive S is filled in the second hole 25 to fix the second wire 5b to the second hole 25, the adhesive agent A is filled in the first hole 24 to fix the first wire 5a to the first hole 24, and so on. Therefore, operability of the second embodiment is better than that of the first embodiment.

The basket type grasping forceps 1A according to the embodiment exhibit the same effect as the basket type grasping forceps 1 described in the first embodiment.

Third Embodiment

Figure 8:
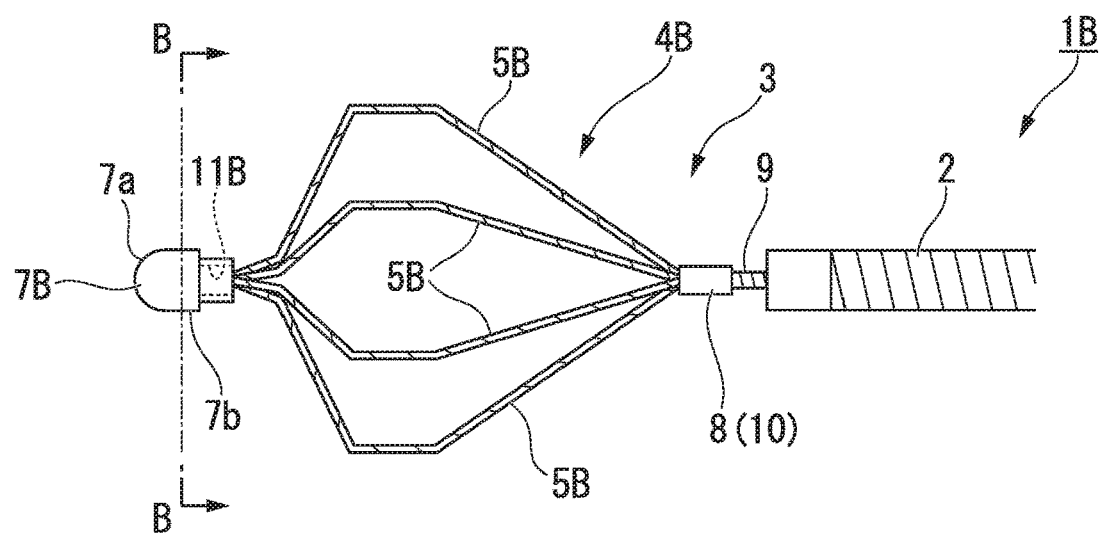
FIG. 8 is a side view showing a distal portion of basket type grasping forceps according to a third embodiment of the present invention.
Figure 9:
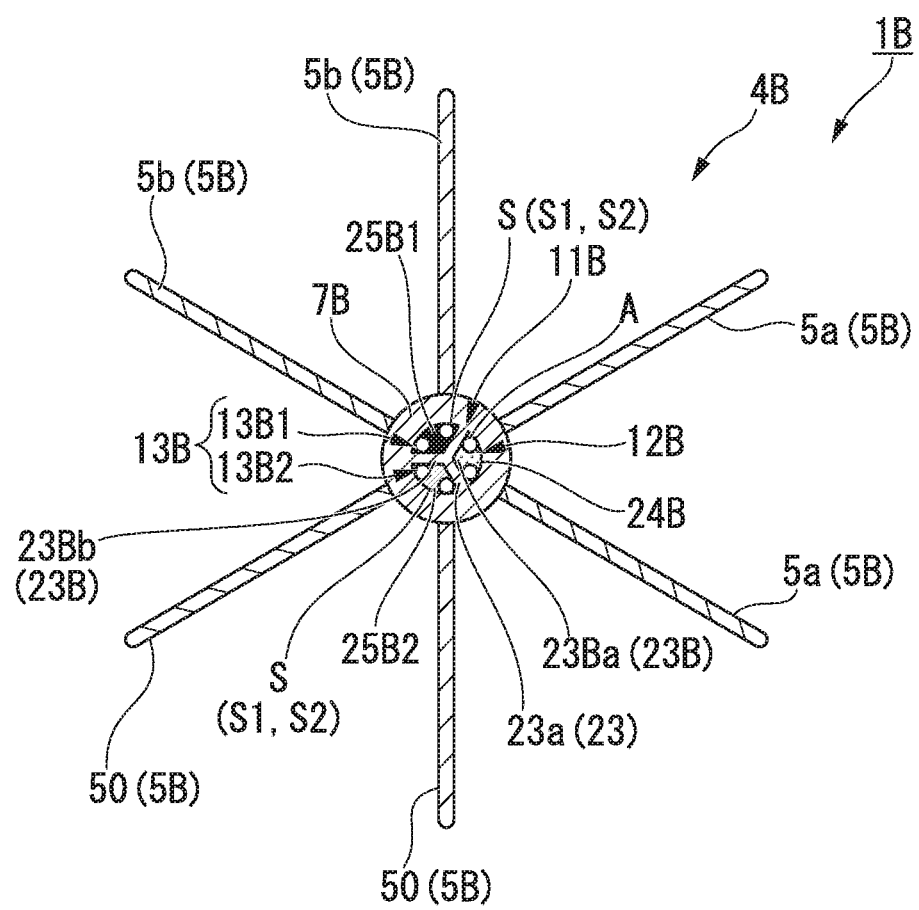
FIG. 9 is a cross-sectional view taken along line B-B of FIG. 8.

Next, a third embodiment of the present invention will be described. In the embodiment, the same reference numerals as the first and second embodiments designate components that are common in shapes or functions to the components described in the first and second embodiments, and overlapping description thereof will be omitted. FIG. 8 is a side view showing a distal portion of basket type grasping forceps 1B according to the embodiment. FIG. 9 is a cross-sectional view taken along line B-B of FIG. 8.

As shown in FIGS. 8 and 9, the basket type grasping forceps 1B includes a basket section 4B having a configuration that differs from the basket section 4 described in the first embodiment.

The basket section 4B includes basket wires 5B having a configuration that differs from the basket wires 5 described in the first embodiment. The basket section 4B includes a distal fixing member 7B having a shape different from the distal fixing member 7 described in the first embodiment. Further, like the first embodiment, the basket wires 5B of the embodiment are fixed to the proximal fixing member 8 described in the first embodiment.

The basket wires 5B include the first wire 5a and the second wire 5b described in the first embodiment, and a third wire 50 different from both of the first wire 5a and the second wire 5b. The basket section 4B of the embodiment includes two first wires 5a that are adjacent to each other, two second wires 5b that are adjacent to each other, and two third wires 50 that are adjacent to each other.

The third wire 50 has a configuration that differs from the second wire 5b in that the third wire 50 is fixed to a second high-strength fixing section 13B2 (to be described below). A material and a shape of the third wire 50 may be the same as the second wire 5b.

The distal fixing member 7B has the same distal end portion 7a and the same outer circumferential portion 7b as the first embodiment, and includes a hole section 11B having a configuration that differs from the hole section 11 described in the first embodiment.

The hole section 11B includes a wire-fixing section 12B, a high-strength fixing section 13B and a partition section 23B. Like the second embodiment, the first wire 5a is fixed to the wire-fixing section 12B. The second wire 5b and the third wire 50 are fixed to the high-strength fixing section 13B. The partition section 23B partitions the wire-fixing section 12B and the high-strength fixing section 13B.

The partition section 23B includes a first partition wall 23Ba and a second partition wall 23Bb. The first partition wall 23Ba partitions the wire-fixing section 12B and the high-strength fixing section 13B. The second partition wall 23Bb partitions the high-strength fixing section 13B into a first high-strength fixing section 13B1 and the second high-strength fixing section 13B2. The distal fixing member 7B has three independent through-holes in the first partition wall 23Ba and the second partition wall 23Bb. Accordingly, the basket wires 5B may be easily fixed to the distal fixing member 7B by filling the adhesive agent A or the solder adhesive S in the through-holes.

Like the first hole 24 described in the second embodiment, the wire-fixing section 12B has a hole (a first hole 24B) independent from the high-strength fixing section 13B. A distal end of the first wire 5a is inserted into the first hole 24B as the wire-fixing section 12B. Further, in the embodiment, the adhesive agent A is filled in the first hole 24B. Accordingly, in the embodiment, the first wire 5a and the distal fixing member 7B are fixed to the first hole 24B by the adhesive agent A. The adhesive agent A is, for example, the same epoxy-based adhesive agent A as the first and second embodiments.

The high-strength fixing section 13B includes the first high-strength fixing section 13B1 to which the second wire 5b is fixed, and the second high-strength fixing section 13B2 to which the third wire 50 is fixed.

Like the second hole 25 described in the second embodiment, the first high-strength fixing section 13B1 has a hole (a second hole 25B1) independent from the wire-fixing section 12B. A distal end of the second wire 5b is inserted into the second hole 25B1 as the first high-strength fixing section 13B1. Further, in the embodiment, the solder adhesive S is filled in the second hole 25B1 as the first high-strength fixing section 13B1. Accordingly, in the embodiment, the second wire 5b and the distal fixing member 7B are fixed to the second hole 25B 1 serving as the first high-strength fixing section 13B1 by the solder adhesive S. Like the first and second embodiments, the solder adhesive S is, for example, the brazing material S1 or the solder S2.

The second high-strength fixing section 13B2 is a portion of to which the third wire 50 is fixed more strongly than the fixing strength of the second wire 5b with the first high-strength fixing section 13B1.

The second high-strength fixing section 13B2 has a through-hole (a second hole 25B2) passing through the distal fixing member 7B and having a size into which the third wire 50 is capable of being inserted. The second hole 25B2 as the second high-strength fixing section 13B2 is a hole independent from the wire-fixing section 12B.

The fixing means with respect to each of the basket wires 5B in each of the wire-fixing section 12B, the first high-strength fixing section 13B1 and the second high-strength fixing section 13B2 is selected according to combinations of the materials of the distal fixing member 7B and each of the basket wires 5B such that the fixing strength of the first high-strength fixing section 13B1 with respect to the second wire 5b is higher than the fixing strength of the wire-fixing section 12B with respect to the first wire 5a, and the fixing strength of the second high-strength fixing section 13B2 with respect to the third wire 5o is higher than the fixing strength of the first high-strength fixing section 13B1 with respect to the second wire 5b.

In the basket type grasping forceps 1B according to the embodiment, by a force pulling out each of the basket wires 5B from the distal fixing member 7B, first, the two first wires 5a are removed from the wire-fixing section 12B, and then, the two second wires 5b adjacent to the first wires 5a are removed from the first high-strength fixing section 13B1. As the first wires 5a and the second wires 5b are removed from the distal fixing member 7B and four wires of the six basket wires 5B are opened at the distal end of the basket section 4B, an opening larger than that of the first embodiment is generated.

If the foreign substances X is possible to remove in a state in which the two first wires 5a are removed from the wire-fixing section 12B and the two second wires 5b are fixed to the first high-strength fixing section 13B1, the two second wires 5b may be fixed to the first high-strength fixing section 13B1.

The basket type grasping forceps 1B according to the embodiment also exhibit the same effect as the basket type grasping forceps 1 described in the first embodiment.

In the embodiment, since the distal ends of the first wires 5a and the second wires 5b that are adjacent to each other are removed from the distal fixing member 7B in this order, a large opening can be formed at the distal portion of the basket section 4B and the foreign substances X can be removed easily in comparison with the case in which the basket wires 5 are randomly removed at the distal portion of the basket section 4B.

Further, in the embodiment, the six basket wires 5B may be configured to be withdrawn from the distal fixing member 7B one by one. For example, when the six basket wires 5B are seen from the distal side toward the proximal side of the basket section 4B, the six basket wires 5B may be configured to be sequentially removed in one direction along an arc about a central portion of the basket section 4B. The basket wires 5B may be configured to be removed such that the opening of the basket section 4B is gradually widened from the basket wire 5B which has the smallest fixing strength with respect to the distal fixing member 7B among the six basket wires 5B as a starting point. Such a configuration contributes to the generation of the large opening in the distal portion of the basket section 4B when the number of the basket wires 5B is four or more.

Fourth Embodiment

Figure 10:
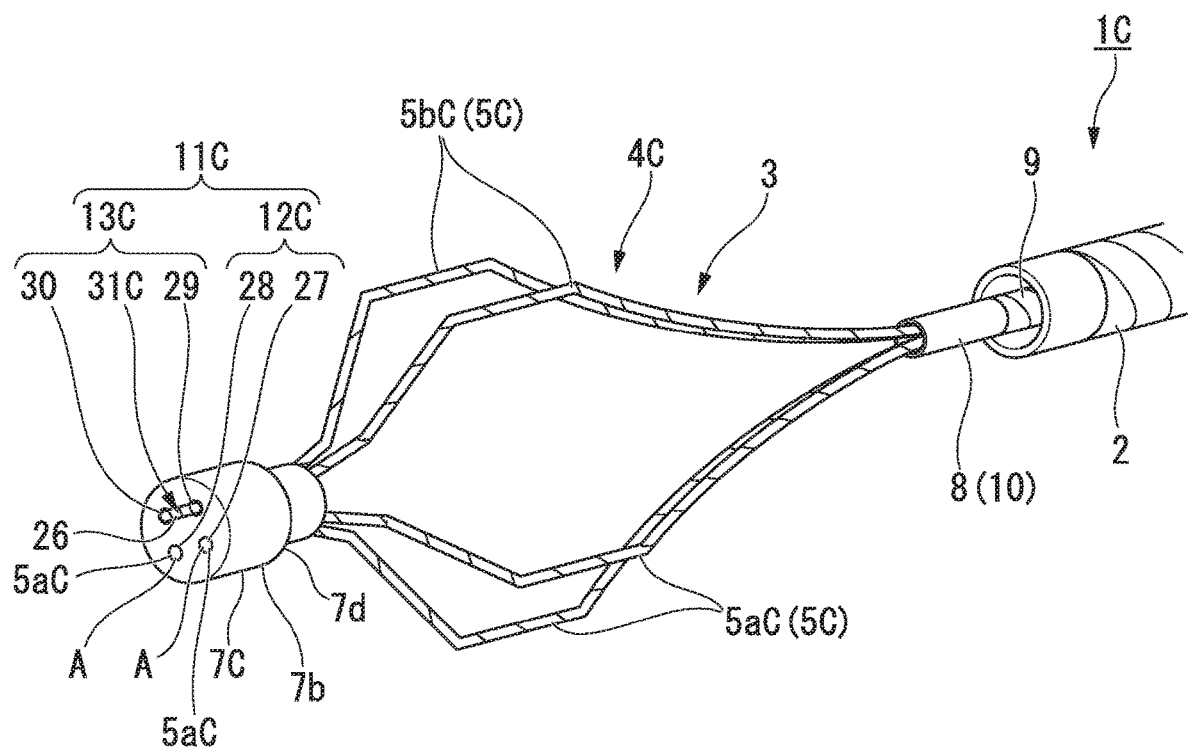
FIG. 10 is a perspective view showing a distal portion of basket type grasping forceps according to a fourth embodiment of the present invention.

Next, a fourth embodiment of the present invention will be described. In the embodiment, the same reference numerals as used in the embodiments designate components that are common in shapes or functions to the components described in the embodiments, and overlapping description thereof will be omitted. FIG. 10 is a perspective view showing a distal portion of basket type grasping forceps 1C according to the embodiment.

As shown in FIG. 10, the basket type grasping forceps 1C includes a basket section 4C having a configuration that differs from the basket section 4 described in the first embodiment.

The basket section 4C includes basket wires 5C and a distal fixing member 7C having configurations different from the basket wires 5 and the distal fixing member 7 described in the first embodiment.

The basket wires 5C include first wires 5aC identical to the first wire 5a described in the first embodiment, and one second wire 5bC having a configuration that differs from the second wire 5b described in the first embodiment.

The second wire 5bC is a continuous wire extending from the proximal fixing member 8 to the distal side, having a folded portion 26 at the distal end of the distal fixing member 7C and returning to the proximal fixing member 8. The second wire 5bC has the same elasticity as the first wire 5a and constitutes a portion of the basket shape that is expandable and contractible.

The basket section 4C of the embodiment is constituted by the first wire 5aC and the second wire 5bC in a basket shape.

Since the folded portion 26 is engaged with a distal end surface of the distal fixing member 7C, in regard to a strength resisting against a force pulling the second wire 5bC to the proximal side of the distal fixing member 7C, the second wire 5bC can be fixed to the distal fixing member 7C more strongly than the first wire 5aC.

The distal fixing member 7C includes the same outer circumferential portion 7b and the same stepped section 7d as the first embodiment. The distal fixing member 7C includes a hole section 11C having a configuration that differs from the hole section 11 described in the first embodiment.

The hole section 11C has a wire-fixing section 12C and a high-strength fixing section 13C. The wire-fixing section 12C has a plurality of through-holes (a first through-hole 27 and a second through-hole 28) to which a plurality of first wires 5aC is fixed. The high-strength fixing section 13C has a plurality of through-holes (a third through-hole 29 and a fourth through-hole 30) to which the second wire 5bC is fixed.

In the embodiment, the first through-hole 27, the second through-hole 28, the third through-hole 29 and the fourth through-hole 30 are spaced from each other and pass through the distal fixing member 7C.

In the wire-fixing section 12C, both of the first wire 5aC inserted into the first through-hole 27 and the first wire 5aC inserted into the second through-hole 28 are fixed by the adhesive agent A.

Further, the number of through-holes formed in the wire-fixing section 12C may be appropriately increased or decreased according to the number of the first wires 5aC in the basket wires 5C.

The high-strength fixing section 13C fixes the second wire 5bC and the distal fixing member 7C by using a fixing means having a strength larger than the fixing strength between the first wire 5aC and the distal fixing member 7C. Since the second wire 5bC comes in contact with the distal end surface of the distal fixing member 7C to engage therewith, the high-strength fixing section 13C and the second wire 5bC are not separated until one of the distal fixing member 7C and the second wire 5bC is broken. In the embodiment, a portion disposed between the opening of a distal end of the third through-hole 29 and the opening of a distal end of the fourth through-hole 30 at the distal end surface of the distal fixing member 7C is a locking portion 31C of the high-strength fixing section 13C to which the second wire 5bC is locked. That is, in the embodiment, the folded portion 26 of the second wire 5bC and the locking portion 31C in the distal fixing member 7C are provided as a means configured to fix the second wire 5bC and the distal fixing member 7C in a state in which the fixing strength is larger than the fixing strength between the first wire 5aC and the distal fixing member 7C.

In the embodiment, the strength of breaking one of the distal fixing member 7C and the second wire 5bC is larger than the strength of adhering the first wire 5aC being inserted into the first through-hole 27 or the second through-hole 28 and being adheared by using the adhesive agent A.

An action of the basket type grasping forceps 1C according to the embodiment will be described.

In the embodiment, the folded portion 26 of the second wire 5bC connects the openings of the distal end sides of the third through-hole 29 and the fourth through-hole 30 that constitute the high-strength fixing section 13C. That is, the second wire 5bC is returned to the distal side of the distal end surface of the distal fixing member 7C and is inserted through the openings of the third through-hole 29 and the fourth through-hole 30 of the distal end surface of the distal fixing member 7C. Further, the second wire 5bC is returned to the distal end surface of the distal fixing member 7C to extend to the proximal fixing member 8 through the third through-hole 29 and the fourth through-hole 30.

The fixing strength between the second wire 5bC and the distal fixing member 7C is larger than the fixing strength between the first wire 5aC and the distal fixing member 7C. For this reason, in the embodiment, the first wire 5aC is removed from the distal fixing member 7C earlier than the second wire 5bC when the same external forces to pulling out the first wire 5aC and the second wire 5bC from the distal fixing member 7C is applied to the first wire 5aC and the second wire 5bC. As a result, an opening for removing the foreign substances X from the basket section 4C is generated while the second wire 5bC and the distal fixing member 7C hold the fixed state.

Fifth Embodiment

Figure 11:
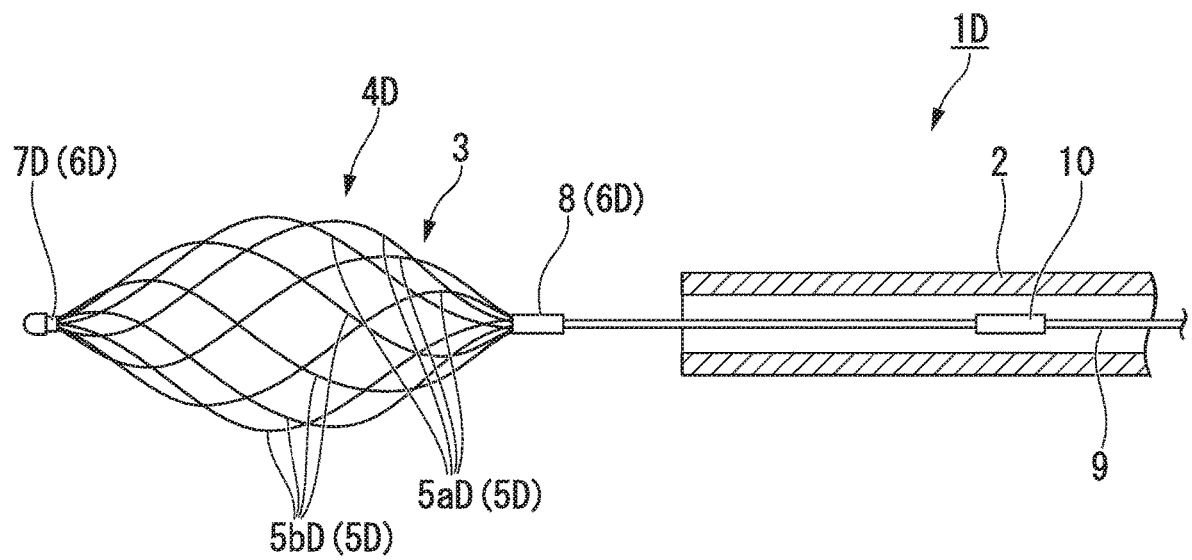
FIG. 11 is a partial cross-sectional view showing a distal portion of basket type grasping forceps according to a fifth embodiment of the present invention.
Figure 12:
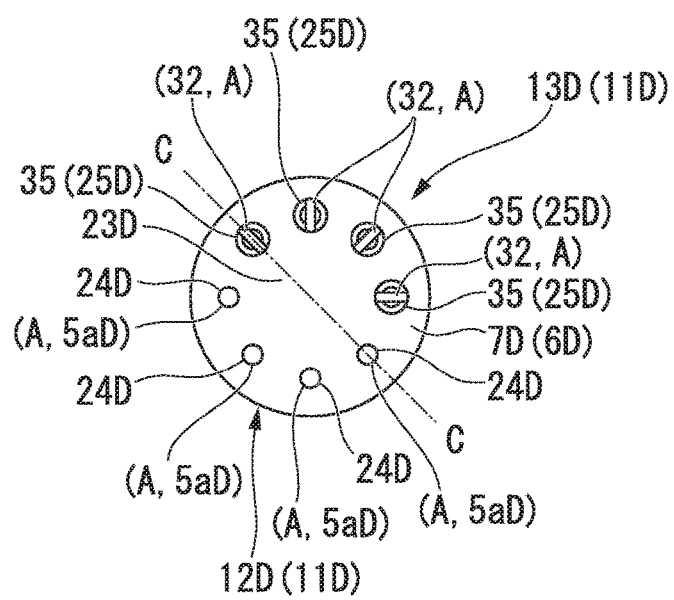
FIG. 12 is a front view showing the basket type grasping forceps according to the fifth embodiment of the present invention.
Figure 13:
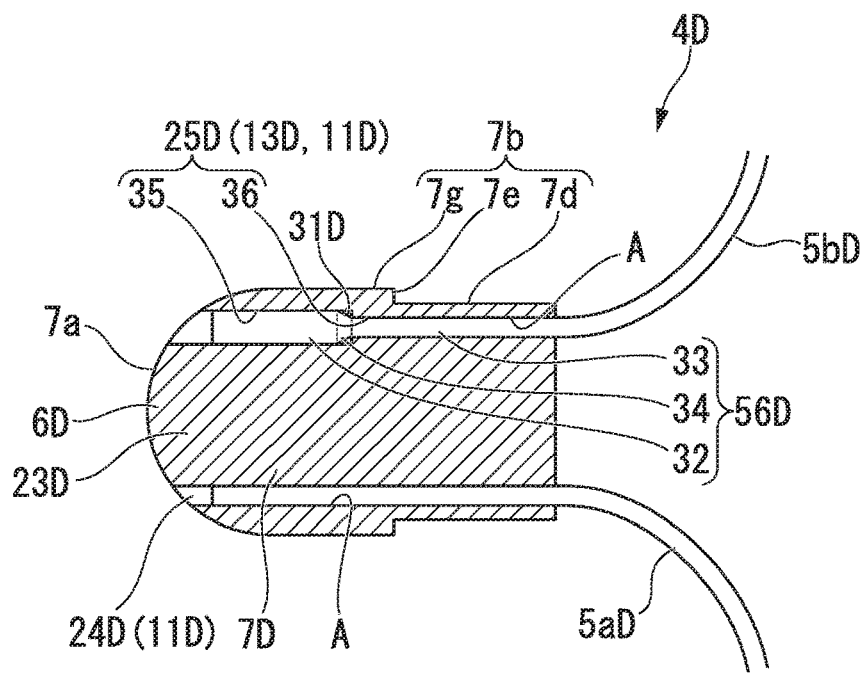
FIG. 13 is a cross-sectional view taken along line C-C of FIG. 12.

Next, a fifth embodiment of the present invention will be described. In the embodiment, the same reference numerals as used in the embodiments designate components that are common in shapes or functions to the components described in the embodiments, and overlapping description thereof will be omitted. FIG. 11 is a partial cross-sectional view showing a distal portion of basket type grasping forceps 1D according to the embodiment. FIG. 12 is a front view of the basket type grasping forceps 1D according to the embodiment. FIG. 13 is a cross-sectional view taken along line C-C of FIG. 12.

As shown in FIG. 11, the basket type grasping forceps 1D include a basket section 4D having a configuration that differs from the basket section 4 described in the first embodiment.

The basket section 4D includes basket wires 5D having a configuration that differs from the basket wires 5 described in the first embodiment. The basket section 4D includes a distal fixing member 7D having a configuration that differs from the distal fixing member 7 described in the first embodiment. Further, like the first embodiment, the basket wires 5D of the embodiment is fixed to the proximal fixing member 8. In addition, in the embodiment, the basket wires 5D pass through the proximal fixing member 8 to further extend to the proximal side, and is fixed to the connecting member 10 that is separately provided from the proximal fixing member 8. In the embodiment, the basket section 4D and the manipulation wire 9 are fixed by the connecting member 10.

The basket wires 5D have first wires 5aD and second wires 5bD that form a helical shape. In the embodiment, the basket wires 5D have four first wires 5aD and four second wires 5bD.

The first wires 5aD form a helical shape about a straight line that connects the proximal fixing member 8 and the distal fixing member 7D, and are fixed to the proximal fixing member 8 and the distal fixing member 7D to form a substantially fusiform shape having a maximum diameter at a substantially intermediate portion between the proximal fixing member 8 and the distal fixing member 7D.

The second wires 5bD form a helical shape about the straight line that connects the proximal fixing member 8 and the distal fixing member 7D, and are fixed to the proximal fixing member 8 and the distal fixing member 7D to form a substantially fusiform shape having a maximum diameter at a substantially intermediate portion between the proximal fixing member 8 and the distal fixing member 7D.

Further, as shown in FIG. 13, the second wire 5bD has a large diameter wire section 32, a reference diameter section 33 and a stepped section 34. The large diameter wire section 32 has a relatively larger diameter than the reference diameter section 33 at the distal end. The reference diameter section 33 has the same diameter as the outer diameter of the first wire 5aD at the proximal side of the large diameter wire section 32. The stepped section 34 forms a boundary between the large diameter wire section 32 and the reference diameter section 33.

Both of the first wire 5aD and the second wire 5bD are formed of a nickel-titanium alloy, and have superelasticity that maintains a predetermined helical shape.

The large diameter wire section 32 is an area formed at a distal end of the second wire 5bD, and has a maximum outer diameter larger than the reference diameter section 33 by crushing to be flattened in a cross-sectional shape of the second wire 5bD.

The reference diameter section 33 is a circular cross-sectional area having a diameter smaller than the maximum outer diameter of the large diameter wire section 32. The reference diameter section 33 is formed in the vicinity of the large diameter wire section 32 at the proximal side of the large diameter wire section 32. The reference diameter section 33 has a function of forming a substantially fusiform basket in the basket section 4D and holding the foreign substances X like the first wire 5aD.

The stepped section 34 is formed at the second wire 5bD in order to strongly fix the second wire 5bD to the distal fixing member 7D by locking the stepped section 34 to the distal fixing member 7D.

As shown in FIG. 12, the distal fixing member 7D in a fixing member 6D has a hole section 11D into which the first wire 5aD and the second wire 5bD of the embodiment are inserted, instead of the hole section 11 described in the first embodiment.

The hole section 11D includes a wire-fixing section 12D and a high-strength fixing section 13D. The first wires 5aD are fixed to each through-holes of the wire-fixing section 12D like the fourth embodiment, respectively. In the high-strength fixing section 13D, the second wires 5bD are fixed to each of through-holes of the high-strength fixing section 13D, unlike the high-strength fixing section 13 described in the first embodiment.

Through-holes (first holes 24D) are formed in the wire-fixing section 12D corresponding to the number of the first wires 5aD. Like the first embodiment, the first wires 5aD are fixed to the first holes 24D by the adhesive agent A (see FIG. 11). When the distal fixing member 7D is seen from the distal end side toward the proximal end side, as shown in FIG. 12, the plurality of first holes 24D of the embodiment are disposed in parallel with gaps in the circumferential direction. The first holes 24D are adjacent to each other.

As shown in FIG. 12, through-holes (second holes 25D) corresponding to the number of the second wires 5bD are formed in the high-strength fixing section 13D. The second wires 5bD are fixed to the second holes 25D. When the distal fixing member 7D is seen from the distal end side toward the proximal end side, a plurality of second holes 25D of the embodiment are disposed with gaps in the circumferential direction. The second holes 25D are adjacent to each other.

Each of the second holes 25D formed in the high-strength fixing section 13D have a large diameter hole section 35 and a small diameter hole section 36. The large diameter wire section 32 of the second wire 5bD is disposed in the large diameter hole section 35. The small diameter hole section 36 is disposed adjacent to the large diameter hole section 35 at the proximal side of the large diameter hole section 35, and the reference diameter section 33 of the second wire 5bD is inserted into the small diameter hole section 36. A stepped difference is formed at a boundary between the large diameter hole section 35 and the small diameter hole section 36. The small diameter hole section 36 has a dimension such that although the reference diameter section 33 of the second wire 5bD can advance and retract, the large diameter wire section 32 of the second wire 5bD cannot enter. In the embodiment, the stepped difference formed at the boundary between the large diameter hole section 35 and the small diameter hole section 36 is a locking portion 31D to which the stepped section 34 formed at the second wire 5bD is locked.

In the embodiment, as the second wire 5bD is inserted from the reference diameter section 33 side from the distal side toward the proximal side of the distal fixing member 7D, the stepped section 34 disposed at the boundary between the large diameter wire section 32 and the reference diameter section 33 is configured to be locked to a step of the distal end side of the small diameter hole section 36. Further, in a state in which the second wire 5bD is attached to the high-strength fixing section 13D, the adhesive agent A is filled in the distal end portion of the large diameter hole section 35, and the second wire 5bD and the high-strength fixing section 13D are also fixed by adhesion.

In the embodiment, the wire-fixing section 12D and the high-strength fixing section 13D are through-holes formed in the distal fixing member 7D. The partition section 23D configured to partition the wire-fixing section 12D and the high-strength fixing section 13D is formed between the wire-fixing section 12D and the high-strength fixing section 13D.

The basket type grasping forceps 1D according to the embodiment also exhibit the same effect as the basket type grasping forceps 1 described in the first embodiment.

In the embodiment, both of the first wire 5aD and the second wire 5bD as the basket wires 5D are formed of a nickel-titanium alloy, and are hard to fix to the distal fixing member 7D by brazing. However, while the first wire 5aD is fixed to the distal fixing member 7D by only an adhesive force due to the adhesive agent, since the second wire 5bD is fixed by locking the stepped section 34 to the distal end surface of the small diameter hole section 36 in addition to the adhesive agent, the first wire 5a is configured to be removed before the second wire 5b.

Sixth Embodiment

Figure 14:
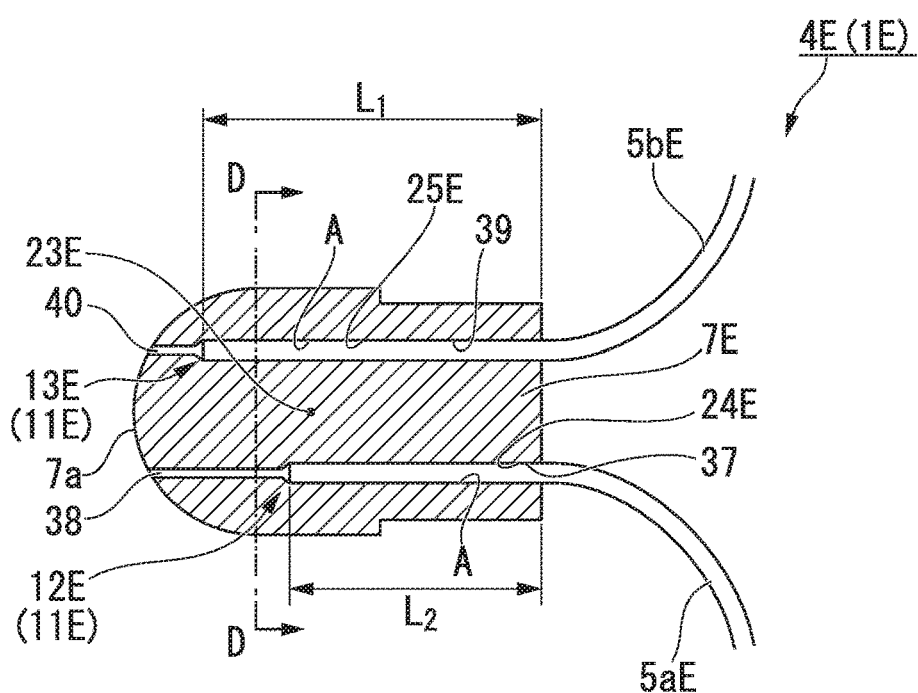
FIG. 14 is a cross-sectional view taken along the same line as the line C-C of FIG. 12, showing a distal portion of basket type grasping forceps according to a sixth embodiment of the present invention.
Figure 15:
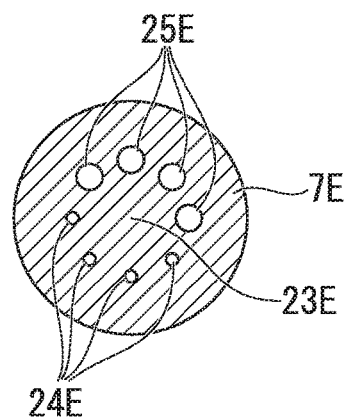
FIG. 15 is a cross-sectional view of a distal fixing member taken along line D-D of FIG. 14.

Next, a sixth embodiment of the present invention will be described. In the embodiment, the same reference numerals as used in the embodiments designate components that are common in shapes or functions to the components described in the embodiments, and overlapping description thereof will be omitted. FIG. 14 is a cross-sectional view taken along line C-C of FIG. 12, showing a distal portion of basket type grasping forceps 1E according to the embodiment. FIG. 15 is a cross-sectional view of a distal fixing member 7E taken along line D-D of FIG. 14.

As shown in FIG. 14, a basket section 4E having a configuration that differs from the basket section 4 described in the first embodiment is provided.

The basket section 4E includes basket wires 5E having a configuration that differs from the basket wires 5 described in the first embodiment. That is, in the embodiment, the basket wires 5E include a first wire 5aE and a second wire 5bE. The first wire 5aE forms a helical shape like the basket wires 5D described in the fifth embodiment. The second wire 5bE is longer than the second wire 5bD described in the fifth embodiment at the distal portion. The basket section 4E includes a distal fixing member 7E instead of the distal fixing member 7 described in the first embodiment. Distal end portions of the first wire 5aE and the second wire 5bE of the embodiment are fixed to the distal fixing member 7E.

In the second wire 5bE, the shape of a portion of the basket section 4E that constitutes an intermediate portion of the basket shape is substantially the same as the first wire 5aE, and only a length of the distal end portion is larger than the first wire 5aE.

Like the first embodiment, proximal end portions of the first wire 5aE and the second wire 5bE are fixed to the proximal fixing member 8 described in the first embodiment.

As shown in FIGS. 14 and 15, the distal fixing member 7E includes hole sections 11E and a partition section 23E. The hole sections 11E include a wire-fixing section 12E (a first hole 24E) to which the first wire 5aE is fixed, and a high-strength fixing section 13E (a second hole 25E) to which the second wire 5bE is fixed. The partition section 23E partitions the wire-fixing section 12E and the high-strength fixing section 13E.

The hole sections 11E of the distal fixing member 7E are through-holes formed on the first wire 5aE and the second wire 5bE, respectively. The partition section 23E is formed between the first hole 24E to which the first wire 5aE is fixed and the second hole 25E to which the second wire 5bE is fixed.

The wire-fixing section 12E includes a first concave section 37 and a first flow path 38. The first wire 5aE is inserted from a proximal side of the first concave section 37. The first flow path 38 comes in communication with the first concave section 37 and is opened at a distal end surface of the distal fixing member 7E.

The first concave section 37 is a concave section into which a distal end of the first wire 5aE is inserted to a predetermined depth from the proximal side toward the distal side. The first concave section 37 has a large diameter such that a slight clearance is provided with respect to the outer diameter of the first wire 5aE.

The first flow path 38 is a flow path configured to discharge an excess portion of the adhesive agent A for fixing the first wire 5aE to the first concave section 37.

The high-strength fixing section 13E includes a second concave section 39 and a second flow path 40. The second wire 5bE is inserted into the second concave section 39 from the proximal side. The second flow path 40 comes in communication with the second concave section 39 and is open at the distal end surface of the distal fixing member 7E.

A distal end of the second concave section 39 is disposed closer to the distal side than a distal end of the first concave section 37. For this reason, an insertion depth of the second wire 5bE into the second concave section 39 is larger than an insertion depth of the first wire 5aE into the first concave section 37.

The second flow path 40 is a flow path configured to discharge an excess portion of the adhesive agent A for fixing the second wire 5bE to the second concave section 39.

In the embodiment, both of the first wire 5aE and the second wire 5bE are fixed to the distal fixing member 7E by the adhesive agent A. The second wire 5bE comes in contact with an inner surface of the second concave section 38 at an area larger than that of the first wire 5aE, and has a fixing strength larger than that of the first wire 5aE as a whole. For this reason, when a force pulling out the first wire 5aE from the distal fixing member 7E and a force pulling out the second wire 5bE from the distal fixing member 7E are simultaneously applied from the manipulation wire 9, the first wire 5aE is pulled out from the distal fixing member 7E prior to the second wire 5bE.

Accordingly, the basket type grasping forceps 1E according to the embodiment exhibit the same effect as the basket type grasping forceps 1 of the first embodiment.

In the embodiment, since the same fixing method can be employed with respect to the first wire 5aE and the second wire 5bE, the basket type grasping forceps 1E has better manufacturing efficiency than that of the basket type grasping forceps 1 of the first embodiment.

Seventh Embodiment

Figure 16:
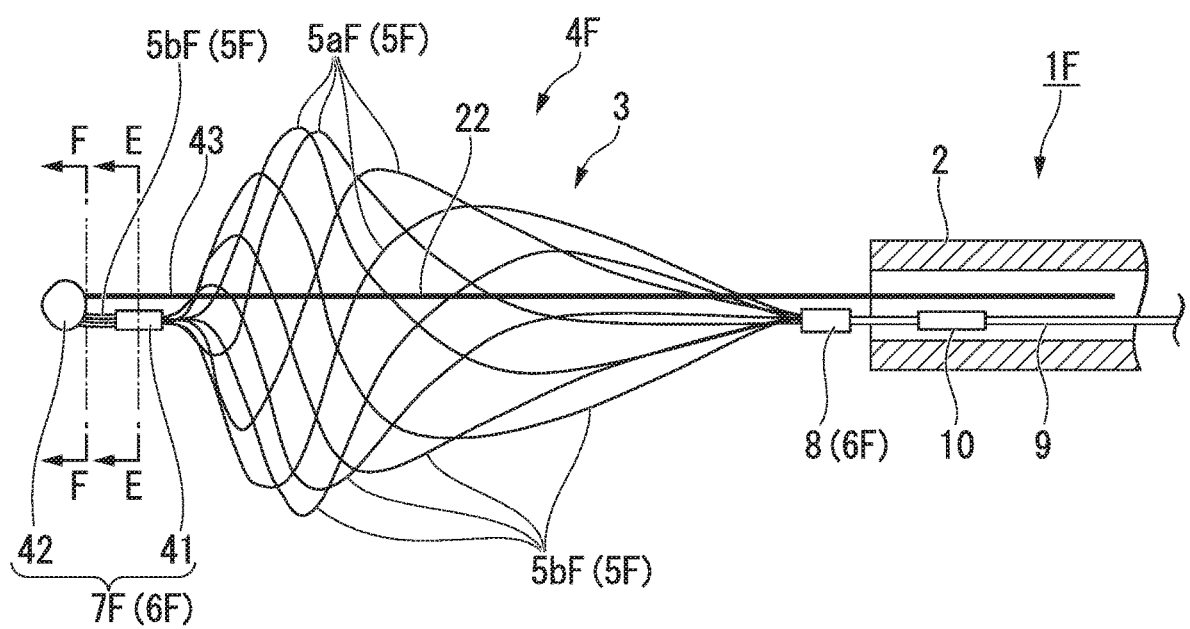
FIG. 16 is a partial cross-sectional view showing a distal portion of basket type grasping forceps according to a seventh embodiment of the present invention.
Figure 17:
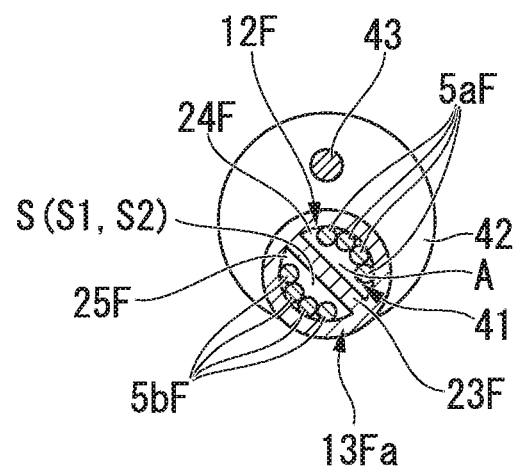
FIG. 17 is a cross-sectional view taken along line E-E of FIG. 16.
Figure 18:
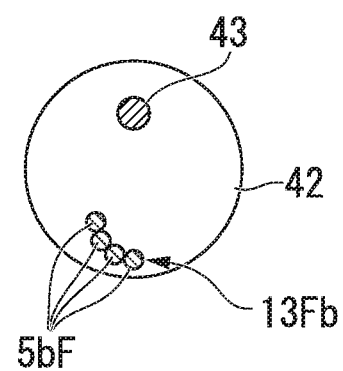
FIG. 18 is a cross-sectional view taken along line F-F of FIG. 16.

Next, a seventh embodiment of the present invention will be described. In the embodiment, the same reference numerals as used in the embodiments designate components that are common in shapes or functions to the components described in the embodiments, and overlapping description thereof will be omitted. FIG. 16 is a partial cross-sectional view showing a distal portion of basket type grasping forceps 1F according to the embodiment. FIG. 17 is a cross-sectional view taken along line E-E of FIG. 16. FIG. 18 is a cross-sectional view taken along line F-F of FIG. 16.

As shown in FIG. 16, the basket type grasping forceps 1F includes a basket section 4F having a configuration that differs from the basket section 4 described in the first embodiment.

The basket section 4F includes basket wires 5F having a helical shape like the basket wires 5D described in the fifth embodiment, instead of the basket wires 5 described in the first embodiment.

The basket wires 5F include the same first wire 5aF as the first wire 5aD described in the fifth embodiment, and a second wire 5bF having a configuration that differs from the second wire 5bD and the distal end portion described in the fifth embodiment.

A distal end of the first wire 5aF is fixed to a first distal fixing member 41 (to be described below) by the adhesive agent A.

A distal end of the second wire 5bF is fixed to the first distal fixing member 41 and a second distal fixing member 42 (to be described below) by the solder adhesive S.

As shown in FIG. 16, the fixing member 6F includes the proximal fixing member 8 described in the first embodiment, and a distal fixing member 7F having a configuration that differs from the distal fixing member 7 described in the first embodiment.

The proximal fixing member 8 of the embodiment fixes base ends of the first wire 5aF and the second wire 5bF like the first embodiment.

The distal fixing member 7F includes the first distal fixing member 41 and the second distal fixing member 42. The first distal fixing member 41 is disposed at a distal side of the basket section 4F. The second distal fixing member 42 is disposed at a farther distal side of the first distal fixing member 41.

As shown in FIG. 17, the first distal fixing member 41 is fixed to the first wire 5aF and the second wire 5bF that constitute the basket wires 5F. The first distal fixing member 41 includes a wire-fixing section 12F, a high-strength fixing section 13Fa and a partition section 23F. The first wire 5aF is inserted into the wire-fixing section 12F. The second wire 5bF is inserted into the high-strength fixing section 13Fa. The partition section 23F partitions the wire-fixing section 12F and the high-strength fixing section 13Fa. A hole section 11F of the first distal fixing member 41 is partitioned into a first hole 24F that constitutes the wire-fixing section 12F and a second hole 25F that constitutes the high-strength fixing section 13Fa by the partition section 23F.

The first wire 5aF is fixed to the wire-fixing section 12F by the adhesive agent A.

The second wire 5bF is fixed to the high-strength fixing section 13Fa by the solder adhesive S.

Like the first embodiment, the first distal fixing member 41 may have a structure having a single hole without the partition section 23F.

As shown in FIG. 18, the second distal fixing member 42 has a high-strength fixing section 13Fb to which the second wire 5bF of the basket wires 5F is fixed. The distal end of the second wire 5bF farther extending to the distal side through the high-strength fixing section 13Fa of the first distal fixing member 41 is fixed to the second distal fixing member 42 by the solder adhesive S.

In addition, in the embodiment, as shown in FIGS. 16 and 18, a distal end of a center wire 43 is fixed to the second distal fixing member 42.

As shown in FIG. 16, the center wire 43 extends from the distal end of the basket section 4F toward the proximal side of the basket section 4F. A proximal end of the center wire 43 is disposed in the sheath 2. The center wire 43 is a member configured to support the first wire 5aF and the second wire 5bF at the distal ends of the first wire 5aF and the second wire 5bF such that the first wire 5aF and the second wire 5bF having helical shapes form a substantially fusiform shape.

The fixing strength between the second distal fixing member 42 and the second wire 5bF is equal to or larger than the fixing strength between the second wire 5bF and the first distal fixing member 41.

That is, in the embodiment, the first distal fixing member 41 and the second distal fixing member 42 have the high-strength fixing section 13F configured to fix the second wire 5bF more strongly than a fixation of the first wire 5aF with respect to the wire-fixing section 12.

In the basket type grasping forceps 1F according to the embodiment, when a force pulling out the first wire 5aF and the second wire 5bF from the first distal fixing member 41 is received by a force pulling the manipulation wire 9 to the proximal side, the first wire 5aF is pulled out from the first distal fixing member 41 prior to the second wire 5bF and an opening configured to remove the foreign substances X to the distal portion of the basket section 4F is generated. Here, the second wire 5bF, the first distal fixing member 41, the second distal fixing member 42 and the center wire 43 are integrally connected, and a state in which the first wire 5aF is fixed to the proximal fixing member 8 is maintained. For this reason, no member drops into the body when the first wire 5aF is removed from the first distal fixing member 41.

The basket type grasping forceps 1F according to the embodiment also exhibit the same effect as the basket type grasping forceps 1 described in the first embodiment.

Hereinabove, while the embodiments of the present invention have been described, the technical scope of the present invention is not limited to the embodiments. Changes to combinations of components of the embodiments, various modifications of the components, or deletion thereof may be made without departing from the spirit of the present invention. The present invention is not limited to the above-mentioned description and is only limited by the scope of the accompanying claims.

What is claimed is:

1. A basket type grasping forceps, comprising:
   a sheath;
   a main body section having a distal end and a proximal end, the main body section being inserted through the sheath; and
   a manipulation section fixed to the sheath on the proximal end of the main body section, the main body including:
   a basket section disposed at the distal end side of the main body section and configured to hold foreign substances; and
   a manipulation wire disposed at a proximal end side of the basket section and fixed to the basket section, the basket section including:
   a plurality of basket wires disposed to form a basket shape to hold the foreign substances therein;
   a distal fixing member fixed to the plurality of basket wires at a distal end portion of the basket section; and
   a center wire extending from a distal end of the basket section toward a proximal side of the basket section, the distal fixing member including:
   a wire-fixing section that is fixed to a first wire that is at least one of the plurality of basket wires;
   a high-strength fixing section that is fixed to a second wire that is at least another one of the plurality of basket wires, the high-strength fixing section being fixed to the second wire with a fixing strength that is stronger than a fixing strength of the wire-fixing section with the first wire;
   a first distal fixing member fixed to a distal end section of the basket wire and disposed at a distal side of the basket section; and
   a second distal fixing member that includes the high-strength fixing section and that is fixed distally of the first distal fixing member, at least one of the plurality of basket wires being fixed to the high-strength fixing section, the second distal fixing member being fixed to a distal end of the center wire; and
   wherein the first distal fixing member has a first center, the second distal fixing member has a second center, and the first center is offset from the second center.

2. The basket type grasping forceps according to claim 1, wherein:
   the first distal fixing member includes a hole into which the second wire is insertable, and
   the second wire extends towards the distal end section of the basket section through the hole and is fixed to the second distal fixing member.

3. The basket type grasping forceps according to claim 1, wherein the second wire is exposed between the first distal fixing member and the second distal fixing member.

4. The basket type grasping forceps according to claim 1, wherein
   the distal end of the first wire is fixed to the first distal fixing member by an adhesive agent, and
   the distal end of the second wire is fixed to the second distal fixing member and the high-strength fixing section by a solder adhesive.

5. The basket type grasping forceps according to claim 1, wherein
   when the manipulation wire is pulled, the first wire and the second wire are pulled out from the first distal fixing member such that the first wire is pulled out from the first distal fixing member prior to the second wire.

6. The basket type grasping forceps according to claim 1, wherein
   the distal end of the second wire protrudes from a distal end of the first distal fixing member.

7. The basket type grasping forceps according to claim 1, wherein the distal end of the first wire is spaced apart from the second distal fixing member;
   the second wire extends towards the second distal fixing member through the high-strength fixing section and a distal end of the second wire is fixed to the second distal fixing member;
   a fixing strength of the second distal fixing member with the second wire is equal to or larger than a fixing strength of the high-strength fixing section with the second wire.

* * * * *